(12) United States Patent
Zlatanski et al.

(10) Patent No.: US 11,782,026 B2
(45) Date of Patent: Oct. 10, 2023

(54) TILT AND CURVATURE MEASUREMENTS OF METAL SHEETS IN A ROLLING MILL

(71) Applicant: ABB Schweiz AG, Baden (CH)

(72) Inventors: Martin Zlatanski, Küsnacht (CH); Thomas Wiik, Västerås (SE)

(73) Assignee: ABB Schweiz AG, Baden (CH)

( * ) Notice: Subject to any disclaimer, the term of this patent is extended or adjusted under 35 U.S.C. 154(b) by 0 days.

(21) Appl. No.: 17/652,509

(22) Filed: Feb. 25, 2022

(65) Prior Publication Data
US 2022/0283120 A1 Sep. 8, 2022

(30) Foreign Application Priority Data
Mar. 3, 2021 (EP) ..................................... 21160573

(51) Int. Cl.
*G01N 27/72* (2006.01)
*B21B 38/00* (2006.01)
*G01N 33/20* (2019.01)

(52) U.S. Cl.
CPC ............. *G01N 27/72* (2013.01); *B21B 38/00* (2013.01); *G01N 33/20* (2013.01)

(58) Field of Classification Search
None
See application file for complete search history.

(56) References Cited

U.S. PATENT DOCUMENTS

| | | | |
|---|---|---|---|
| 5,418,457 A | 5/1995 | Hedengren et al. | |
| 5,420,518 A * | 5/1995 | Schafer, Jr. | B22D 46/00 164/4.1 |
| 6,310,476 B1 | 10/2001 | Kawanami et al. | |
| 8,390,280 B2 | 3/2013 | Badoux et al. | |
| 2006/0167650 A1* | 7/2006 | Nagano | H01L 22/20 702/170 |

(Continued)

FOREIGN PATENT DOCUMENTS

| | | |
|---|---|---|
| EP | 3141502 A1 | 3/2017 |
| FR | 2589566 A1 | 5/1987 |
| JP | S60144603 A | 7/1985 |

OTHER PUBLICATIONS

Extended European Search Report; Application No. 21160573.8; Completed: Jul. 22, 2021; dated Aug. 2, 2021; 6 Pages.

*Primary Examiner* — Nasima Monsur
(74) *Attorney, Agent, or Firm* — WHITMYER IP GROUP LLC

(57) ABSTRACT

A measurement device for measuring properties of a metal sheet processed in a rolling mill, including: an inspection coil set including a transmitter coil and a receiver coil, the transmitter coil being configured to apply a time-varying magnetic field to the metal sheet, and the receiver coil being configured to detect a magnetic field transient produced from the metal sheet. The property of the metal sheet is derivable from the magnetic field transient. A correction coil set, for detecting a spatial deviation of the metal sheet from a reference plane, each correction coil being connectable to a capacitor to form a respective resonance circuit having a resonance frequency. The correction coils are resonated at the respective resonance frequency. A shift in the resonance frequency in the presence of the metal sheet is detectable and the spatial deviation is derivable from the shifts.

19 Claims, 6 Drawing Sheets

(56) References Cited

U.S. PATENT DOCUMENTS

2009/0242200 A1* 10/2009 Badoux ................ E21B 47/085
                                                        166/255.2
2013/0328555 A1    12/2013 Krause et al.
2017/0073179 A1*   3/2017 Uno ....................... B65H 7/125

* cited by examiner

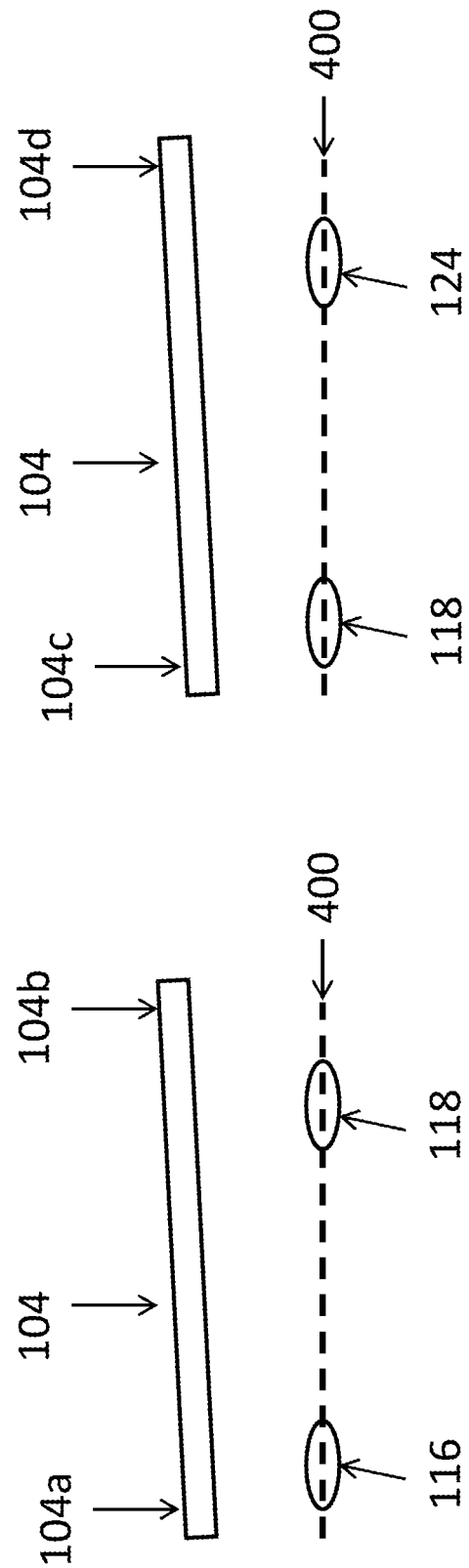

TILT AND CURVATURE MEASUREMENTS OF METAL SHEETS IN A ROLLING MILL

TECHNICAL FIELD

The present invention relates to a measurement device for measuring properties of a metal sheet processed in a rolling mill. The present invention further relates to a rolling mill and to a method for detecting a spatial deviation from a reference plane of a metal sheet processed in a rolling mill.

BACKGROUND

Metal rolling generally relates to producing a metal work piece with reduced and uniform thickness by rolling the metal work piece between two rotating work rolls.

In order to ensure high product quality, the thickness of the work piece is accurately monitored and controlled.

Conventionally used pulsed eddy current measurement technology is based on measuring eddy currents induced in a metal sheet by a rapidly varying magnetic field applied to the metal sheet. Based on the measured eddy currents are e.g., the resistivity and the thickness of the metal sheet extracted.

If the metal sheet is perfectly parallel to the to the sensor, only two coils are needed for accurately measuring the metal sheet properties. However, in reality, the metal sheet will not always be parallel with the sensor whereby metal sheet curvature and tilt with respect to the sensor will affect the measurements and lead to inaccurate estimates of the metal sheet properties.

Accordingly, it is desirable to improve the accuracy of metal sheet measurements in rolling mills.

SUMMARY

In view of the above-mentioned and other drawbacks of the prior art, it is an object of the present invention to provide a measurement device that at least partly alleviates the deficiencies with prior art. The suggested embodiments provide an improved way of detecting spatial deviations such as curvature and tilt of a metal sheet processed in a rolling mill.

According to a first aspect of the invention, there is provided a measurement device for measuring properties of a metal sheet processed in a rolling mill.

The measurement device comprises an inspection coil set comprising a transmitter coil and a receiver coil, the transmitter coil being configured to apply a time-varying magnetic field to the metal sheet, and the receiver coil being configured to detect a magnetic field transient produced from the metal sheet in response to the applied time-varying magnetic field, wherein the at least one property of the metal sheet is derivable from the magnetic field transient.

The measurement device comprises a correction coil set for detecting a spatial deviation of the metal sheet from a reference plane, each correction coil being connectable to a capacitor to form a respective resonance circuit having a resonance frequency, wherein the correction coils are configured to be resonated at the respective resonance frequency, wherein a shift in the resonance frequency in the presence of the metal sheet is detectable, wherein the spatial deviation is derivable from the shifts in resonance frequencies.

The present invention is at least partly based on the realization to measure spatial deviations by correction coils that are resonated at their resonance frequency, and that the resonance frequency is shifted in the presence of a metal sheet.

A frequency shift is a shift in resonance frequency of a resonance circuit comprising a correction coil, where the shift is caused by the inductive contribution from the metal sheet placed in the near proximity of the correction coil. Thus, the nominal resonance frequency of the resonance circuit may firstly be measured or estimated without the presence of the metal sheet, whereby the shift in frequency is a deviation in resonance frequency from the nominal resonance frequency.

For instance, if the metal sheet is not parallel with respect to a reference plane, for example provided by a sensor head or a plane of the correction coils, the inductive component of the resonance circuits of two correction coils differs from each other due to the different inductive contribution of the metal sheet. The frequency shifts of the correction coils will therefore differ from each other, whereby a tilt of the metal sheet can be detected.

With the proposed measurement device, adding additional poles and parasitic capacitance to the inspection coils system can be avoided.

The reference plane may be arbitrarily selected but is preferably parallel to a plane of the correction coils. The main axis of the magnetic field produced by the correction coils may be normal to the reference plane.

Preferably, the correction coils are arranged to minimize coupling and crosstalk with the inspection coils. This can be achieved in various conceivable ways. One way is by arranging the correction coils far from the inspection coils. For example, when the correction coils and the inspection coils share a common support, the correction coils may be placed near the edges or corners of the support and the inspection coils may be placed near the center of the support. Such a support may for example be a carrier substrate that may be planar.

The properties of the metal sheet measured by the inspection coils may be at least one of a distance to a sensor head, resistivity of the metal sheet, and a thickness of the metal sheet.

The spatial deviation of the metal sheet may be at least one of a curvature of the metal sheet and a tilt of the metal sheet. A curvature may for example be a local curvature of the metal sheet.

The inspection coils operate by a measurement technique relying on eddy currents in the metal sheet. The transmitter coil produces a time-varying magnetic field that is applied to the metal sheet. In response, eddy currents are produced in the metal sheet, as a consequence of the applied time-varying magnetic field. The eddy currents are detectable by the receiver coil arranged a distance from the metal sheet. A voltage signal is induced in the receiver coil by the time derivative of the magnetic field produced by the eddy currents in the work item. The voltage signal is processed, such as for example amplified as in often the case in data acquisition systems to produce an acquired signal used for determining the properties of the metal sheet.

The applied time-varying magnetic field is preferably produced by interrupting a bias DC-current in the transmitter coils. Thus, a pulsed magnetic field is applied, and the receiver coil measures the magnetic field generated by the eddy currents in response to the pulse, preferably in response to the negative edge of the pulse when the magnetic field is removed.

Determining the properties may be performed by e.g. theoretical models, or by using empirically determined model that relates time dependencies of eddy current decay to metal sheet properties. Various ways known per se exist for extracting such properties from metal sheets based on inductive measurements, e.g. magnetic transient measurements.

Advantageously, the resonance frequency of the correction coils may be higher than a frequency of the magnetic field transient measured from the metal sheet in response to the applied magnetic field. Hereby, interference between the measurement performed by the inspection coils and the correction coils can be reduced. The resonance frequency of the correction coils with the respective capacitor may be higher than a maximal frequency present in the measured transient from the metal sheet.

Preferably, the resonance frequency of the resonance circuits comprising the correction coils may be at least twice the frequency of the magnetic field transient measured from the metal sheet in response to the applied magnetic field.

Further, the resonance frequency of the resonance circuits comprising the correction coils may be at least three times as high as the frequency of the magnetic field transient measured from the metal sheet in response to the applied magnetic field.

Still further, the resonance frequency of the resonance circuits comprising the correction coils may be at least four times as high as the frequency of the magnetic field transient measured from the metal sheet in response to the applied magnetic field.

Still further, the resonance frequency of the resonance circuits comprising the correction coils may be at least five times as high as the frequency of the magnetic field transient measured from the metal sheet in response to the applied magnetic field.

The frequency of the magnetic field transient measured from the metal sheet depends on the frequency of the applied time-varying magnetic field. Thus, the resonance circuits may be adapted with regards to the frequency of the applied time-varying magnetic field to ensure a desired relationship between the resonance frequency of the resonance circuits comprising the correction coils and the frequency of the magnetic field transient.

In order to further reduce coupling and crosstalk, in embodiments, the correction coils may be spatially separated from transmitter and receiver coils and arranged on the outside of the windings of the transmitter and receiver coils. In order words, the correction coils are arranged outside the inner areas surrounded by the windings of the inspection coils.

The correction coils are placed in areas where they do not substantially intercept the magnetic field generated and captured by the inspection coils and therefore the interaction between the inspection coils and the correction coils is minimized.

In embodiments, the correction coils may be substantially smaller than the transmitter coil and the receiver coil. Hereby, coupling and crosstalk between the correction coils and the inspection coils may be further reduced. Further, a resolution of the spatial deviation measurement may be improved by enabling a more local measurement using the smaller correction coils.

Further, the correction coils may be resonated only when the transmitter coil is in an excitation phase applying a magnetic field to the metal sheet. This advantageously avoids interference between the measurement performed by the inspection coils and the measurement performed by the correction coils.

In embodiments, the spatial deviation of the metal sheet from the reference plane may be detected by comparing frequency shifts to each other. For example, by comparing relative shifts between two or more corrections coils a tilt of the metal sheet is detectable. By analyzing the frequency shifts of three or more resonated correction coils a curvature of the metal sheet can be detected. The frequency shifts are preferably acquired for the same time instant to provide an instant picture of the tilt and/or curvature of the metal sheet.

In embodiments, the transmitter and receiver coils may be planar coils. The planar inspection coils may share the same plane.

In embodiments, the correction coils may be planar coils. The planar correction coils may share the same plane.

The planar correction coils and the planar inspection coils may share the same plane.

Planar coils provide for a cost-efficient measurement device that allows for planar designs on for example printed circuit boards.

In embodiments, the measurement device may comprise a carrier substrate for supporting the inspection coils and the carrier coils. The carrier substrate may be a printed circuit board.

In embodiments, the measurement device may be connectable to a control unit configured to: control a supply of electric signal to the correction coils at the resonance frequency, detect the shift in the resonance frequency in the presence of the metal sheet, and derive the spatial deviation based on the detected shift.

According to a second aspect of the invention, there is provided a rolling mill comprising at least two working rolls configured to process a metal sheet therebetween, and a measurement device according to embodiments discussed herein.

Further effects and features of the second aspect of the invention are largely analogous to those described above in connection with the first aspect of the invention.

According to a third aspect of the invention, there is provided a method for detecting a spatial deviation from a reference plane of a metal sheet processed in a rolling mill, the metal sheet being subject to a measurement by a transmitter coil and a receiver coil configured to perform a magnetic field transient measurement for determining at least one property of the metal sheet, the method comprising: resonating each of a set of correction coils connected to a respective capacitor, at a respective resonance frequency, detecting a shift in the resonance frequency in the presence of the metal sheet for each correction coil, whereby the spatial deviation is derivable from the shifts in resonance frequencies.

In embodiments, the method may comprise resonating the correction coils only when the transmitter coil is not applying a applying a time-varying magnetic field to the metal sheet for performing the magnetic field transient measurement. In other words, the correction coils are only resonated in the absence of the time-varying magnetic field applied by the transmitter coil. Thus, the correction coils are advantageously resonated for performing their correction measurement in time windows when the transmitter coil is not applying the time-varying magnetic field and the receiver coils are not measuring the eddy current response from the metal sheet. The correction coils may for example be resonated prior to triggering a metal sheet inspection measurement performed by the inspection coils, or after the altered magnetic field is removed. Hereby, interference between the measurement performed by the transmitter coil and the receiver coils and the spatial deviation measurement performed by the correction coils can be reduced or avoided.

Further effects and features of the third aspect of the invention are largely analogous to those described above in connection with the first aspect and the second aspect of the invention.

There is further provided a control unit configured to: control a supply of electric signal to correction coils at the resonance frequency, the correction coils being arranged for detecting a spatial deviation of the metal sheet from a reference plane, each correction coil being connectable to a capacitor to form a respective resonance circuit having a resonance frequency, wherein the correction coils are configured to be resonated at the respective resonance frequency, wherein a shift in the resonance frequency in the presence of the metal sheet is detectable, wherein the spatial deviation is derivable from the shifts in resonance frequencies, detect the shift in the resonance frequency in the presence of the metal sheet, and derive the spatial deviation based on the detected shift.

Further features of, and advantages with, the present invention will become apparent when studying the appended claims and the following description. The skilled person realize that different features of the present invention may be combined to create embodiments other than those described in the following, without departing from the scope of the present invention.

BRIEF DESCRIPTION OF THE DRAWINGS

These and other aspects of the present invention will now be described in more detail, with reference to the appended drawings showing an example embodiment of the invention, wherein:

FIGS. 4A-4B each conceptually illustrates a tilted metal sheet with respect to a reference plane;

DETAILED DESCRIPTION

In the present detailed description, various embodiments of the present invention are herein described with reference to specific implementations. In describing embodiments, specific terminology is employed for the sake of clarity. However, the invention is not intended to be limited to the specific terminology so selected. While specific exemplary embodiments are discussed, it should be understood that this is done for illustration purposes only. A person skilled in the relevant art will recognize that other components and configurations can be used without parting from the scope of the invention.

Figure 1:
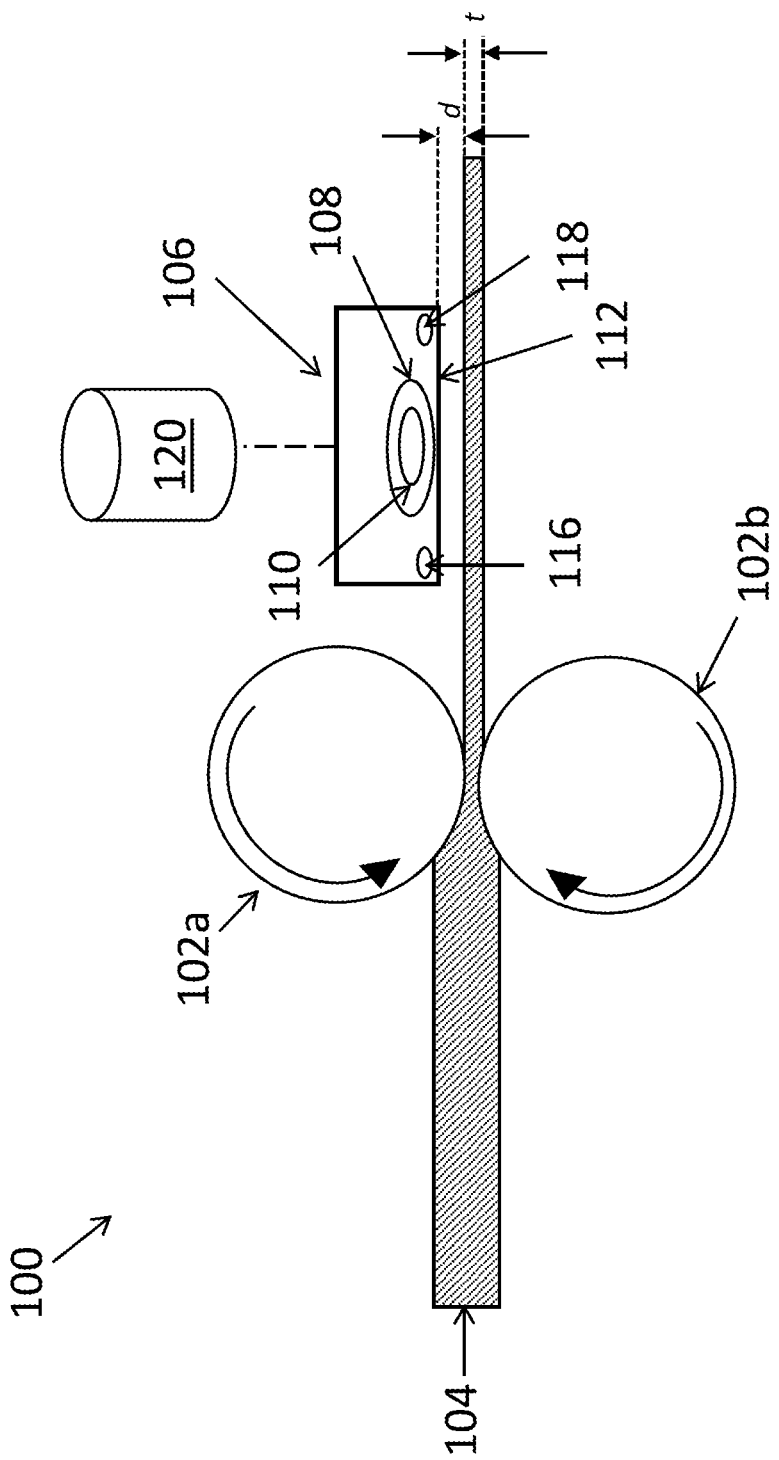
FIG. 1 conceptually illustrates a metal sheet being processed in a rolling mill according to an embodiment of the invention.

FIG. 1 conceptually illustrates a rolling mill 100 comprising a set of work rolls 102a and 102b adapted to process a metal sheet 104. The work rolls 102a-b rotate while the metal sheet 104 is being fed between the work rolls 102a-b. The work rolls 102a-b reduces the thickness of the work item, as is appreciated by those skilled in the art. In FIG. 1, a cross-section of the metal sheet 104 is shown.

As the metal sheet 104 is processed in the rolling mill 100, it is desirable to accurately measure properties of the moving metal sheet 104. For this, a measurement device 106 is provided. The measurement device 106 comprises an inspection coil set comprising a transmitter coil 108 and a receiver coil 110. The transmitter coil 108 is configured to apply a time-varying magnetic field to the metal sheet 104. The receiver coil 110 is configured to detect a magnetic field transient produced by eddy currents in the metal sheet 104 generated in response to the applied magnetic field. The properties of the metal sheet are derivable from the magnetic field transient. Such properties may be a distance d to a sensor head 112, resistivity of the metal sheet 104, and a thickness, t, of the metal sheet 104.

As the metal sheet 104 moves, i.e. rolls on the production line from left to right in FIG. 1, it will not be always parallel to the sensor head 112. Metal sheet curvature and tilt with respect to the sensor head will affect the readings and lead to wrong estimates of the distance, resistivity, and thickness. To address this issue the measurement device 106 comprises a correction coil set comprising correction coils 116 and 118 in this example embodiment. The correction coils 116 and 118 are configured for detecting a spatial deviation of the metal sheet 104 from a reference plane. Each correction coil 116, 118 being connectable to a capacitor to form a respective resonance circuit having a resonance frequency. The measurement device 106 may comprise more than two correction coils, such as for example three or more correction coils, as will be apparent with reference to subsequent drawings. In FIG. 1, is only two correction coils 116, 118 shown.

As will be discussed further, the correction coils 116, 118 are configured to be resonated at the respective resonance frequency, wherein a shift in the resonance frequency in the presence of the metal sheet 104 is detectable, wherein the spatial deviation is derivable from the shifts in resonance frequencies. Preferably, the measurement device 106 comprises at least three correction coils.

Generally, the measurement device 106 is adapted to measure the properties of the metal sheet by means of eddy current technology. Thus, the transmitter coil 108 receives an electric current from a current or voltage source, for example as controlled by a control unit 120, to generate and apply a time-varying magnetic field, i.e. a pulsed magnetic field, in the metal sheet 104. The receiver coil 110 detects the resulting magnetic field produced by eddy currents in the metal sheet 104. The control unit 120 receives a signal indicative of the detected magnetic field from which the control unit 120 can derive the properties of the metal sheet 104.

The measurement device 106 is here arranged downstream of the work rolls 102a-b. However, the measurement device 106 may of course be arranged elsewhere, such as upstream of the work rolls 102a-b.

The control unit 120 is communicatively connected, either wirelessly or hardwired, with the measurement device 106 such that the control unit 120 can receive data signals from the measurement device 106. In some embodiments, the control unit 120 is configured to control a supply of electric signal to the correction coils at the resonance frequency, detect the shift in the resonance frequency in the presence of the metal sheet, and derive the spatial deviation based on the detected shift.

Figure 2:
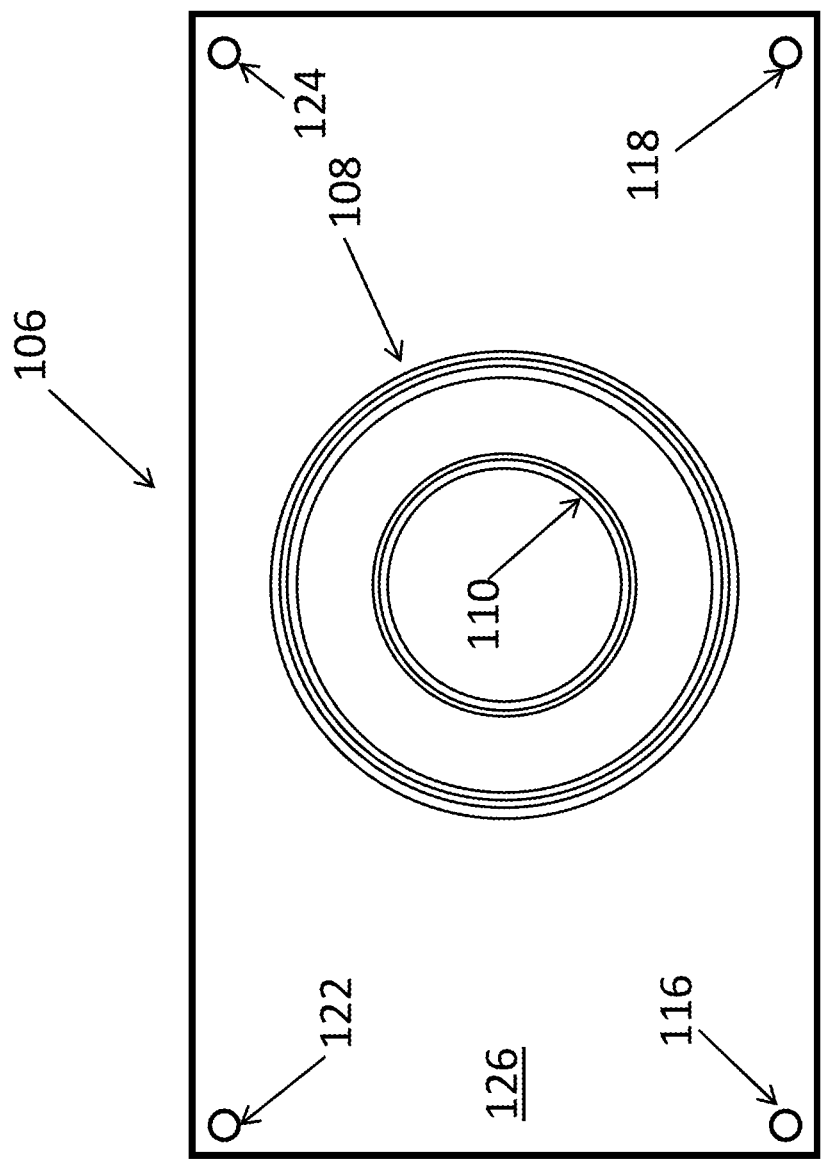
FIG. 2 conceptually illustrates a measurement device according to embodiments of the invention.

FIG. 2 conceptually illustrates a measurement device 106 according to example embodiments. The measurement device 106 comprises the transmitter coil 108 and the receiver coil 110, here concentrically arranged on a carrier substrate 126 supporting the coils 108, 110. Further, a set of correction coils 116, 118, 122, 124 are also arranged on the substrate 126. In other words, in this embodiment, a carrier substrate 126 is included for supporting the inspection coils 108, 110 and the correction coils 116, 118, 122, 124. Further, the carrier substrate 126 may support on-chip capacitors (not shown) forming the resonance circuits with the correction coils 116, 118, 122, 124. The capacitor forming the resonance circuits with the correction coils may be comprised in the measurement device 106.

Further, in the present embodiment, the transmitter and receiver coils 108, 110 are planar coils. Additionally, the correction coils 116, 118, 122, 124 are planar coils. A planar coil generally has its windings in a plane providing for a relatively "flat" coil with its height being a single or only a few wire-layers.

Preferably, the correction coils are arranged to be substantially decoupled from the inspection coils. In the shown embodiment in FIG. 2, this is obtained by arranging the correction coils 116, 118, 122, 124 as far from the inspection coils 108 and 110 as possible. The inspection coils 108 and 110 are arranged in the center of the carrier substrate 126 and the correction coils 116, 118, 122, 124 are arrange far to the sides of the substrate, here close to the corners of the substrate 126.

Further, the correction coils 116, 118, 122, 124 are spatially separated from the transmitter coil 108 and the receiver coil 110 and arranged on the outside of the windings of the transmitter and receiver coils. In other words, the correction coils 116, 118, 122, 124 are not arranged inside the cores, surrounded by the windings of the transmitter coil 108 and the receiver coil 110. In some possible implementations, the correction coils 116, 118, 122, 124, are arranged in the same plane, which may be parallel to the reference plane, or which may serve as the reference plane. In this example embodiment, the correction coils 116, 118, 122, 124, the transmitter coil 108 and the receiver coil 110 are arranged in the same plane. This plane may be parallel to the reference plane from which a spatial deviation of the metal sheet is detected. The transmitter coil produces its time-varying magnetic field along a main axis normal to the plane of the substrate 126 and normal to the reference plane.

It should be understood that other arrangements for decoupling the correction coils from the inspection coils are conceivable. For example, the correction coils may be arranged on separate carrier substrates which allows for arranging the correction coils far from the inspection coils with larger degree of freedom compared to having them on the same carrier substrate. However, using a single carrier substrate as shown in FIG. 2 provides for an integrated measurement device provided as a single piece which is easily installed.

With further reference to FIG. 2, the correction coils 116, 118, 122, 124, are substantially smaller than the transmitter coil 108 and the receiver coil 110. The size here refers to an outer diameter of the coils.

Figure 3:
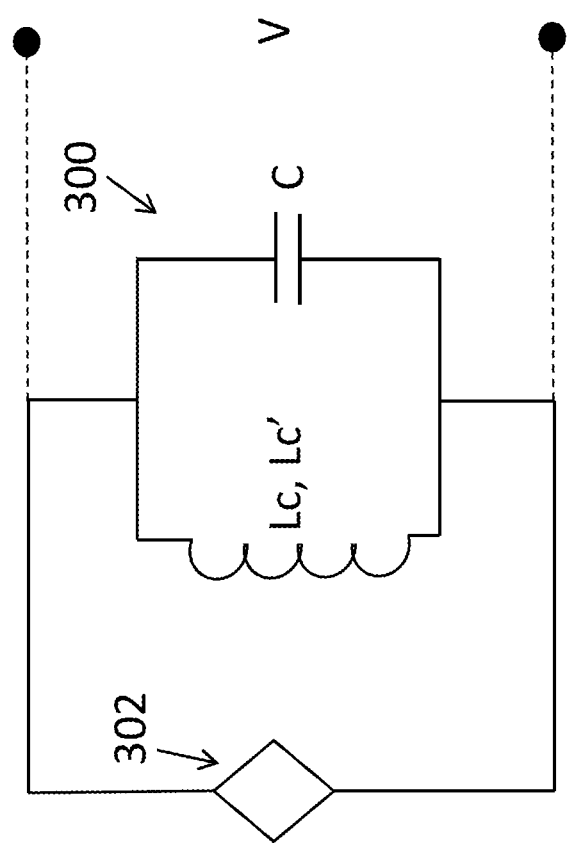
FIG. 3 schematically illustrate an equivalent circuit of a resonance circuit according to embodiments of the invention.

The measurement principle of the correction coils relies on measuring a shift in resonance frequency. FIG. 3 schematically illustrate an equivalent circuit of one such resonance circuit 300.

The circuit 300 is connected to a voltage/current source 302 for driving the circuit 300 at its resonance frequency and a voltage sensor measures the voltage V across the circuit 300. The source 302 may be an alternating current source. The circuit 300 is represented by a capacitor with capacitance C connected in parallel with an inductor Lc which is the inductance of a correction coil with no metal sheet present near the correction coil. In such case, the resonance frequency is proportional to $$\frac{1}{\sqrt{C*Lc}}.$$

Thus, during operation the resonance circuit 300 comprising a correction coil connected with a capacitor C will be driven at its resonance frequency $$\frac{1}{\sqrt{C*Lc}}.$$

The capacitor may be provided in the form of a chip capacitor on the carrier substrate, such as for example a NP0 chip capacitor.

The correction coils and/or the capacitor are designed such that the resonance frequency of the resonance circuit is higher than a frequency of the magnetic field transient measured from the metal sheet in response to the applied magnetic field produced by the transmitter coil. The resonance frequency of the resonance circuit is at least twice the frequency of the magnetic field transient measured from the metal sheet in response to the applied magnetic field.

When the metal sheet is present near the correction coil, an additional inductance, Lm (not shown), contributes to the inductance in the circuit. This is the inductance contribution of the metal sheet, e.g. the metal sheet 104 illustrated in FIG. 1. If the metal sheet is perfectly planar, i.e. with no curvature and with no tilt, the inductance contribution Lm will be the same for all correction coils, whereby also the frequency shift for each correction coil will be substantially the same. However, as is often the case, the metal sheet has some curvature or tilt whereby the inductance contribution Lm will not be equal for all the correction coils. The difference in the overall inductance causes a shift in the resonance frequency for each of the correction coils, which generally is proportional to $$\frac{1}{\sqrt{C*Lc'}},$$

where Lc' is the combined inductance contributions from the metal sheet, Lm, and the correction coils, Lc. Generally, Lc'<Lc.

The spatial deviation of the metal sheet from the reference plane may be detected by comparing resonance frequency shifts to each other as will be conceptually described with reference to FIGS. 4A-4D.

FIG. 4A conceptually illustrates a side view of a tilted metal sheet 104 with respect to a reference plane 400. The metal sheet 104 is here, in FIG. 4A, for clarity shown with no curvature. The correction coils 116 and 118 are shown to be arranged in the reference plane 400, but the reference plane may be elsewhere. The tilted metal sheet 104 is closer to the reference plane 400 at one end 104a than at the other end 104b. If the shift in resonance frequency for the coil 118 is compared to the shift in resonance frequency for the coil 116, the relative shift therebetween, e.g. a ratio between the shift for coil 116 and the shift for coil 118, or a difference between the shifts, provides an indication of a tilt of the metal sheet 104.

FIG. 4A illustrates a side-view where the coils 116 and 118 from FIG. 2 are represented. Note that an analogous description applies if another side view is considered, for example as illustrated in FIG. 4B, where instead a side-view showing correction coils 118 and 124 is presented. Here, the tilted metal sheet 104 is closer to the reference plane 400 at end 104c than at the other end 104d. If the shift in resonance frequency for the coil 118 is compared to the shift in resonance frequency for the coil 124, the relative shift therebetween provides an indication of a tilt of the metal sheet 104.

Figure 4C:
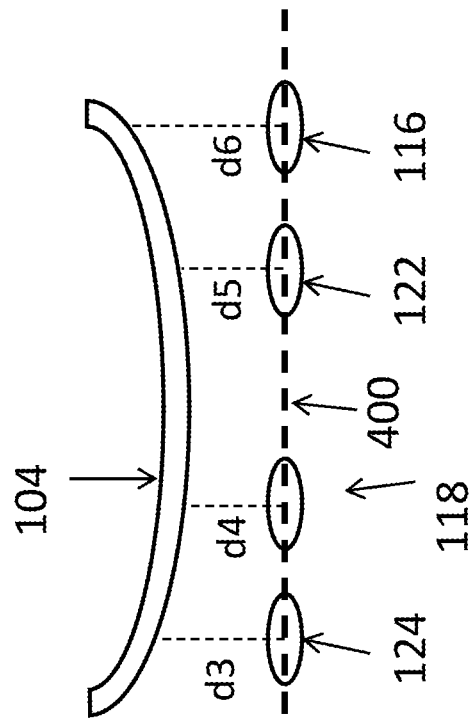
FIGS. 4C-4D each conceptually illustrates a metal sheet with a curvature.

FIG. 4C conceptually illustrates a cross-sectional side-view of a metal sheet 104 with a curvature. In FIG. 4C three correction coils 116, 118, 122 are conceptually illustrated to lie in the reference plane 400. For determining the curvature of the metal sheet, the resonance shift for each of the three coils 116, 122, and 118 is determined. From the three resonance shifts may the curvature be calculated. For example, each of the resonance shifts is indicative of a respective spatial deviation d1, d2, d3 between the sheet, at the location of the correction coils, and the reference plane 400. The three spatial deviations d1, d2, d3, or the resonance shifts indicative thereof, may be used for determining the local curvature of the metal sheet. This is similar to determining the curvature of a path, where at least three points of the path need to be known for determining the curvature.

Figure 4D:
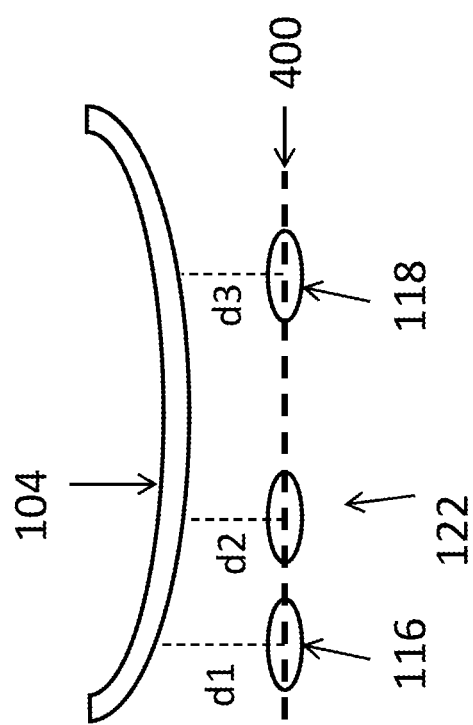

FIG. 4D conceptually illustrates another cross-sectional side-view of a metal sheet 104 with a curvature, here considering four conceptually illustrated correction coils 116, 118, 122, 124. As above, the curvature of the metal sheet 104 may be determined from the resonance shift for each of the correction coils 116, 118, 122, and 118. Each of the resonance shifts is indicative of a respective spatial deviation d3, d4, d5, and d6 between the metal sheet 104, at the location of the respective correction coil, and the reference plane 400. The four spatial deviations d3, d4, d5, and d6, or the resonance shifts indicative thereof, may be used for determining the local curvature of the metal sheet.

As described above, the spatial deviation of the metal sheet is at least one of a curvature of the metal sheet and a tilt of the metal sheet 104.

The relative shifts in resonance frequency between two or more resonance circuits, each including a correction coil, may be compared to pre-stored data relating curvature data and tilt data to resonance frequency shifts. For example, a look-up table may comprise a large number of resonance frequency shift data versus curvature data and tilt data, such that, based on measured frequency shifts, may a control unit find matching, or at least nearly matching curvature data and tilt data.

Another conceivable way to obtain the curvature data and tilt data is by means of empirical models where a large amount of resonance frequency shift data and corresponding curvature data and tilt data are used to build a model.

Another conceivable way to obtain the curvature data and tilt data is by means of machine learning models being taught on prior learning data resonance frequency shift data and corresponding curvature data and tilt data.

Theoretical models are also conceivable to obtain the curvature data and tilt data.

It is further understood that the curvature and tilt may be determined by a combination of two or more of the above-mentioned ways including look-up table, empirical models, theoretical models, and machine learning methods.

Once curvature and/or tilt of a metal sheet is determined, they can be used to correct the properties of the metal sheet measured by the inspection coils in ways that are per se known.

Figure 5:
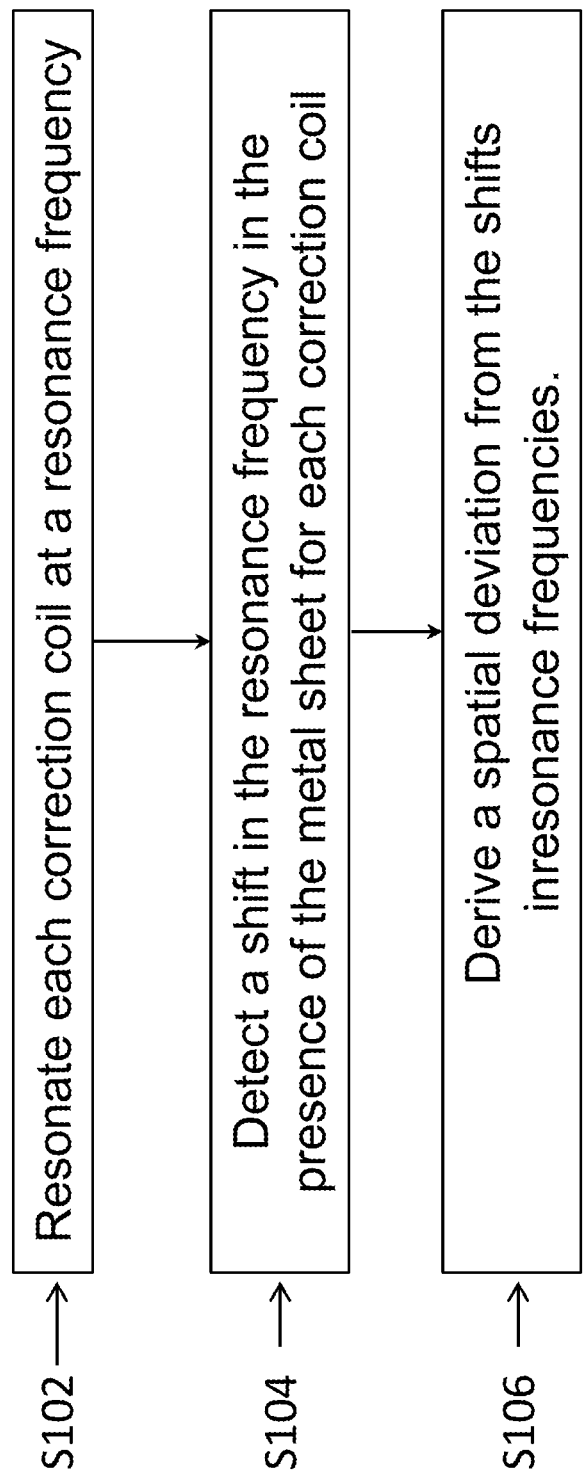
FIG. 5 is a flow-chart of method steps according to embodiments of the invention.

FIG. 5 is a flow-chart of method steps according to embodiments of the present invention. The method is for detecting a spatial deviation from a reference plane of a metal sheet processed in a rolling mill. The metal sheet being subject to a measurement by a transmitter coil and a receiver coil configured to perform a magnetic field transient measurement for determining at least one property of the metal sheet.

The method comprises, in step S102, resonating each of a set of correction coils connected to a respective capacitor, at a respective resonance frequency.

The method further comprises step S104 including, detecting a shift in the resonance frequency in the presence of the metal sheet for each correction coil, whereby the spatial deviation is derivable from the shifts in resonance frequencies in step S106.

Preferably, step S102 of resonating the correction coils is only performed when the transmitter coil is not applying a applying a time-varying magnetic field to the metal sheet for performing the magnetic field transient measurement. Thus, the correction coils are resonated before or after the magnetic field is altered.

A control unit may include a microprocessor, microcontroller, programmable digital signal processor or another programmable device. The control unit may also, or instead, include an application specific integrated circuit, a programmable gate array or programmable array logic, a programmable logic device, or a digital signal processor. Where the control unit includes a programmable device such as the microprocessor, microcontroller or programmable digital signal processor mentioned above, the processor may further include computer executable code that controls operation of the programmable device.

Communication between devices, control units or other modules described herein may be wireless or hardwired as is suitable and implement a suitable protocol for the specific case.

Even though the invention has been described with reference to specific exemplifying embodiments thereof, many different alterations, modifications and the like will become apparent for those skilled in the art.

Additionally, variations to the disclosed embodiments can be understood and effected by the skilled person in practicing the claimed invention, from a study of the drawings, the disclosure, and the appended claims. In the claims, the word "comprising" does not exclude other elements or steps, and the indefinite article "a" or "an" does not exclude a plurality. The mere fact that certain measures are recited in mutually different dependent claims does not indicate that a combination of these measures cannot be used to advantage.

The invention claimed is:

1. A measurement device for measuring properties of a metal sheet processed in a rolling mill, the measurement device comprising:
    an inspection coil set comprising a transmitter coil and a receiver coil,
    the transmitter coil being configured to apply a time-varying magnetic field to the metal sheet, and
    the receiver coil being configured to detect a magnetic field transient produced from the metal sheet in response to the applied time-varying magnetic field, wherein at least one property of the metal sheet is derived from the magnetic field transient, and a correction coil set configured to detect a spatial deviation of the metal sheet from a reference plane, each correction coil being connected to a capacitor to form a respective resonance circuit having a resonance frequency, wherein the correction coils are configured to be resonated at the respective resonance frequency, wherein a shift in the resonance frequency in the presence of the metal sheet is detected, wherein the spatial deviation is derived from the shifts in resonance frequencies.

2. The measurement device according to claim 1, wherein the correction coils are arranged to be substantially decoupled from the inspection coils.

3. The measurement device according to claim 1, wherein the resonance frequency of the resonance circuits is higher than a frequency of the magnetic field transient measured from the metal sheet in response to the applied magnetic field.

4. The measurement device according to claim 3, wherein the resonance frequency of the correction coils is at least twice the frequency of the magnetic field transient measured from the metal sheet in response to the applied magnetic field.

5. The measurement device according to claim 1, wherein the correction coils are spatially separated from the transmitter coil and the receiver coil and arranged on the outside of the windings of the transmitter coil and the receiver coil.

6. The measurement device according to claim 1, wherein the correction coils are substantially smaller than the transmitter coil and the receiver coil.

7. The measurement device according to claim 1, wherein the spatial deviation of the metal sheet is at least one of a curvature of the metal sheet and a tilt of the metal sheet.

8. The measurement device according to claim 1, wherein the spatial deviation of the metal sheet from the reference plane is detected by comparing resonance frequency shifts to each other.

9. The measurement device according to claim 1, wherein the transmitter and receiver coils are planar coils.

10. The measurement device according to claim 1, wherein the correction coils are planar coils.

11. The measurement device according to claim 1, comprising a carrier substrate for supporting the inspection coils set and the correction coils set.

12. The measurement device according to claim 1, connected to a control unit configured to:
control a supply of electric signal to the correction coils at the resonance frequency,
detect the shift in the resonance frequency in the presence of the metal sheet, and
derive the spatial deviation based on the detected shift.

13. The measurement device according to claim 2, wherein the resonance frequency of the resonance circuits is higher than a frequency of the magnetic field transient measured from the metal sheet in response to the applied magnetic field.

14. The measurement device according to claim 2, wherein the correction coils are spatially separated from the transmitter coil and the receiver coil and arranged on the outside of the windings of the transmitter coil and the receiver coil.

15. The measurement device according to claim 2, wherein the correction coils are substantially smaller than the transmitter coil and the receiver coil.

16. The measurement device according to claim 2, wherein the spatial deviation of the metal sheet is at least one of a curvature of the metal sheet and a tilt of the metal sheet.

17. A rolling mill comprising at least two working rolls configured to process a metal sheet therebetween, and a measurement device including:
an inspection coil set including a transmitter coil and a receiver coil,
the transmitter coil being configured to apply a time-varying magnetic field to the metal sheet, and
the receiver coil being configured to detect a magnetic field transient produced from the metal sheet in response to the applied time-varying magnetic field,
wherein at least one property of the metal sheet is derived from the magnetic field transient, and
a correction coil set configured to detect a spatial deviation of the metal sheet from a reference plane, each correction coil being connected to a capacitor to form a respective resonance circuit having a resonance frequency,
wherein the correction coils are configured to be resonated at the respective resonance frequency, wherein a shift in the resonance frequency in the presence of the metal sheet is detected, wherein the spatial deviation is derived from the shifts in resonance frequencies.

18. A method for detecting a spatial deviation from a reference plane of a metal sheet processed in a rolling mill, the method comprising:
measuring the metal sheet with a measurement device; the measurement device including:
an inspection coil set including a transmitter coil and a receiver coil,
the transmitter coil being configured to apply a time-varying magnetic field to the metal sheet, and
the receiver coil being configured to detect a magnetic field transient produced from the metal sheet in response to the applied time-varying magnetic field,
wherein at least one property of the metal sheet is derived from the magnetic field transient, and
a correction coil set configured to detect a spatial deviation of the metal sheet from a reference plane, each correction coil being connected to a capacitor to form a respective resonance circuit having a resonance frequency,
resonating each of the set of correction coils connected to the respective capacitor, at the respective resonance frequency, and
detecting a shift in the resonance frequency in the presence of the metal sheet for each correction coil, whereby the spatial deviation is derived from the shifts in resonance frequencies.

19. The method according to claim 18, comprising resonating the correction coils only when the transmitter coil is not applying a applying a time-varying magnetic field to the metal sheet for performing the magnetic field transient measurement.

* * * * *